United States Patent [19]

Young

[11] 4,049,738

[45] Sept. 20, 1977

[54] SELECTIVE PRODUCTION OF PARA-XYLENE

[75] Inventor: Lewis B. Young, Kendall Park, N.J.

[73] Assignee: Mobil Oil Corporation, New York, N.Y.

[21] Appl. No.: 704,194

[22] Filed: July 12, 1976

[51] Int. Cl.² .......................... C07C 3/52; C07C 15/08; C01B 33/28
[52] U.S. Cl. ............................ 260/671 M; 260/671 C; 423/329
[58] Field of Search ...................... 260/671 M, 671 C

[56] References Cited

U.S. PATENT DOCUMENTS

| 3,965,207 | 6/1976 | Weinstein | 260/671 M |
| 3,965,208 | 6/1976 | Butter et al. | 260/671 M |
| 3,965,209 | 6/1976 | Butter et al. | 260/671 M |
| 3,965,210 | 6/1976 | Chu | 260/671 M |

Primary Examiner—Delbert E. Gantz
Assistant Examiner—J. Thierstein
Attorney, Agent, or Firm—Charles A. Huggett; Raymond W. Barclay

[57] ABSTRACT

Process for the selective production of para-xylene by methylation of toluene in the presence of a catalyst comprising the crystalline aluminosilicate zeolite ZSM-23.

9 Claims, No Drawings

SELECTIVE PRODUCTION OF PARA-XYLENE

BACKGROUND OF THE INVENTION

1. Field of the Invention

This invention relates to a process for the selective production of para-xylene by catalytic methylation of toluene in the presence of a specified crystalline aluminosilicate zeolite catalyst.

2. Description of the Prior Art

Alkylation of aromatic hydrocarbons utilizing crystalline aluminosilicate catalysts has heretofore been described. U.S. Pat. No. 2,904,697 to Mattox refers to alkylation of aromatic hydrocarbons with an olefin in the presence of a crystalline metallic aluminosilicate having uniform pore openings of about 6 to 15 Angstrom units. U.S. Pat. No. 3,251,897 to Wise describes alkylation of aromatic hydrocarbons in the presence of X- or Y-type crystalline aluminosilicate zeolites, specifically such type zeolites wherein the cation is rare earth and/or hydrogen. U.S. Pat. No. 3,751,504 to Keown et al. and U.S. Pat. No. 3,751,506 to Burress describe vapor phase alkylation of aromatic hydrocarbons with olefins, e.g. benzene with ethylene, in the presence of a ZSM-5 type zeolite catalyst.

The alkylation of toluene with methanol in the presence of a cation exchanged zeolite Y has been described by Yashima et al. in the Journal of Catalysis 16, 273–280 (1970). These workers reported selective production of para-xylene over the approximate temperature range of 200 to 275° C., with the maximum yield of para-xylene in the mixture of xylenes, i.e. about 50 percent of the xylene product mixture, being observed at 225° C. Higher temperatures were reported to result in an increase in the yield of meta-xylene and a decrease in production of para and ortho-xylenes.

While the above-noted prior art is considered of interest in connection with the subject matter of the present invention, the methylation process described herein carried out in the presence of a crystalline aluminosilicate zeolite which, in unmodified form, has been found to achieve unexpectedly high selective production of para-xylene has not, insofar as is known, been heretofore described.

Of the xylene isomers, i.e. ortho-, meta- and para-xylene, the latter is of particular value being useful in the manufacture of terephthalic acid which is an intermediate in the manufacture of synthetic fibers such as "Dacron". Mixtures of xylene isomers either alone or in further admixture with ethylbenzene, generally containing a concentration of about 24 weight percent para-xylene in the equilibrium mixture, have been previously separated by expensive superfraction and multistage refrigeration steps. Such process, as will be realized, has involved high operation costs and has a limited yield.

SUMMARY OF THE INVENTION

In accordance with the present invention, there has been discovered a process for selectively producing para-xylene in preference to meta- or ortho-xylene by reaction of toluene with a methylating agent in the presence of a catalyst comprising the crystalline aluminosilicate zeolite ZSM-23.

It has been found that such zeolite, particularly in the hydrogen or acid form, has the ability, without further modification, to afford selectively high yields of para-xylene when employed as a catalyst in the methylation of toluene.

Compared to a conventional thermodynamic equilibrium xylene mixture in which the para:meta:ortho ratio is approximately 1:2:1, the process described herein affords a xylene product in which para-xylene predominates. The improved yield of para-xylene of greater than 50 percent of the total xylene production, compared with approximately 24 percent equilibrium concentration reduces the cost of production and most important the cost of separation of para-xylene from its isomers which is the most expensive step in the current method employed for producing para-xylene.

DESCRIPTION OF SPECIFIC EMBODIMENTS

It is a particular feature of the present invention that a specific crystalline aluminosilicate zeolite, namely ZMS-23, may be effectively employed, without modification, as a catatlyst in the methylation of toluene to selectively produce para-xylene.

ZSM-23 is described in U.S. application Ser. No. 585,632, filed June 10, 1975, which descriptive matter is hereby incorporated herein by reference. Particularly, ZSM-23 has a composition, expressed in terms of mole ratios of oxides, as follows:

(0.5 to 3.0) $R_2O$ : (0.08 to 0.4) $M_2O$ : $Al_2O_3$ : (40 to 250) $SiO_2$ wherein R is a nitrogen-containing cation derived from pyrrolidine and M is an alkali metal cation. It will be noticed that the ratio $R_2O$ to $Al_2O_3$ may exceed unity in this material probably due to the occlusion of excess pyrrolidine species ($R_2O$) within the zeolite pores.

In a preferred synthesized form, the zeolite has a formula, in terms of mole ratios of oxides and in the anhydrous state, as follows:

(0.7-2.8) $R_2O$ : (.08-.25) $M_2O$ : $Al_2O_3$ : (50-220) $SiO_2$ wherein R is a nitrogen-containing cation derived from pyrrolidine, M is an alkali metal, especially sodium.

The original cations of the as-synthesized ASM-23 can be replaced in accordance with techniques well known in the art, at least in part, by ion exchange with other cations. Preferred replacing cations include metal ions, ammonium ions, hydrogen ions and mixtures thereof. Particularly preferred cations are those which render the zeolite catalytically active. These include hydrogen, rare earth metals, and metals of Groups IIA, IIIB, IVB, VIB, VIII, IB, IIB, IIIA and IVA. In a particularly preferred embodiment, the acid form of ZSM-23 is employed wherein cationic sites are predominately occupied by hydrogen.

The synthetic ZSM-23 zeolite possesses a definite distinguishing crystalline structure whose X-ray diffraction pattern shows substantially the significant lines set forth in Table I.

TABLE I

| d(A) | $I/I_o$ |
|---|---|
| 11.2 ± 0.23 | Medium |
| 10.1 ± 0.20 | Weak |
| 7.87 ± 0.15 | Weak |
| 5.59 ± 0.10 | Weak |
| 5.44 ± 0.10 | Weak |
| 4.90 ± 0.10 | Weak |
| 4.53 ± 0.10 | Strong |
| 3.90 ± 0.08 | Very Strong |
| 3.72 ± 0.08 | Very Strong |
| 3.62 ± 0.07 | Very Strong |
| 3.54 ± 0.07 | Medium |
| 3.44 ± 0.07 | Strong |
| 3.36 ± 0.07 | Weak |
| 3.16 ± 0.07 | Weak |
| 3.05 ± 0.06 | Weak |
| 2.99 ± 0.06 | Weak |
| 2.85 ± 0.06 | Weak |
| 2.54 ± 0.05 | Medium |
| 2.47 ± 0.05 | Weak |
| 2.40 ± 0.05 | Weak |

TABLE I-continued

| d(A) | I/I$_o$ |
|---|---|
| 2.34 ± 0.05 | Weak |

These values were determined using standard techniques.

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less that about 1.5 percent by weight may be used. Thus, the original alkali metal of the zeolite may be replaced by ion exchange with other suitable ions of Groups IB to VIII of the Periodic Table including, by way of example, nickel, zinc, calcium or rare earth metals. Generally, for the purpose of this invention, ZSM-23 will be used in the hydrogen form.

M in the above formula can be one or more of a variety of alkali metal cations, suitably defined as including all alkali metal ions derived from alkali metal oxide or hydroxide as well as alkali metal ions included in alkali metal silicates and aluminates (not including alkali metal salts such as sodium chloride or sodium sulfate which may be derived from neutralization of added inorganic acids such as HCl or $H_2SO_4$ or acid salts such as $Al_2(SO_4)_3$). Non-limiting examples of such suitable alkali metal ions include sodium and potassium.

Zeolite ZSM-23 can be suitably prepared by preparing a solution containing sources of an alkali metal oxide, preferably sodium oxide, pyrrolidine, an oxide of aluminum, an oxide of silicon and water and having a composition, in terms of mole ratios of oxides, falling within the following ranges:

| | Broad | Preferred |
|---|---|---|
| $R^+/R^+ + M^+$ | 0.77–1.0 | 0.87–0.95 |
| $OH^-/SiO_2$ | 0–0.06 | 0.01–0.055 |
| $H_2O/OH^-$ | 200–1000 | 200–620 |
| $SiO_2/Al_2O_3$ | 50–250 | 50–236 | wherein R is an organic nitrogen-containing cation derived from pyrrolidine and M is an alkali metal ion, and maintaining the mixture until crystals of the zeolite are formed. (The quantity of $OH^-$ is calculated only from the inorganic sources of alkali without any organic base contribution). Thereafter, the crystals are separated from the liquid and recovered. Typical reaction conditions consist of heating the foregoing reaction mixture to a temperature above 280° F. to about 400° F. for a period of time of from about 6 hours to about 14 days. A more preferred temperature range is from about 300° F. to about 375° F. with the amount of time at a temperature in such range being from about 24 hours to about 11 days.

The digestion of the gel particles is carried out until crystals form. The solid product is separated from the reaction medium, as by cooling the whole to room temperature, filtering and water washing.

The crystalline product is dried, e.g. at 230° F., for from about 8 to 24 hours. Of course, milder conditions may be employed if desired, e.g. room temperature under vacuum.

The composition for the synthesis of synthetic ZSM-23 can be prepared utilizing materials which can supply the appropriate oxide. Such compositions include aluminates, alumina, silicates, silica hydrosol, silica gel, silicic acid and hydroxides. It will be understood that each oxide component utilized in the reaction mixture for preparing ZSM- b 23 can be supplied by one or more essential reactants and they can be mixed together in any order. For example, sodium oxide can be supplied by an aqueous solution of sodium hydroxide or by an aqueous solution of the suitable silicate; the cation derived from pyrrolidine can be either supplied by pyrrolidine or a salt thereof. The reaction mixture can be prepared either batchwise or continuously Crystal size and crystallization time of the ZSM-23 composition will vary with the nature of the reaction mixture employed.

Synthetic ZSM-23 can have the original cations associated therewith replaced by a wide variety of other cations according to techniques well known in the art. Typical replacing cations include hydrogen, ammonium and metal cations including mixtures thereof.

Typical ion exchange techniques would be to contact the synthetc ZSM-23 zeolite with a salt of the desired replacing cation or cations. Although a wide variety of salts can be employed, particular preference is given to chlorides, nitrates and sulfates.

Representative ion exchange techniques are disclosed in a wide variety of patents including U.S. Pat. No. 3,140,249; 3,140,251; and 3,140,253.

Following contact with the salt solution of the desired replacing cation, the zeolite is then preferably washed with water and dried at a temperature ranging from 150° F. to about 600° F. and thereafter is calcined in air or other inert gas at temperatures ranging from about 500° F. to 1500° F. for periods of time ranging from 1 to 48 hours or more to produce a catalytically-active thermal decomposition product thereof.

Regardless of the cations replacing the alkali metal in the synthesized form of the ZSM-23, the special arrangement of the aluminum, silicon and oxygen atoms which form the basic crystal lattice of ZSM-23 remains essentially unchanged by the described replacement of alkali metal as determined by taking an X-ray powder diffraction pattern of the ion-exchanged material.

Prior to use, the above-described zeolite catalyst is calcined in an inert atmosphere, e.g. helium or in an oxygen-containing atmosphere, e.g. air. Calcination takes place at a temperature in the approximate range of 500° to 700° C. and preferably between 450° and 550° C.

In practicing the desired methylation process it may be desirable to incorporate the zeolite in another material resistant to the temperatures and other conditions employed in the methylation process. Such matrix materials include synthetic or naturally occurring substances as well as inorgnic materials such as clay, silica and/or metal oxides. The latter may be either naturally occurring or in the form of gelatinous precipitates or gels including mixtures of silica and metal oxides. Naturally occurring clays which can be composited with the modified zeolite include those of the montmorillonite and kaoline families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the modified zeolites employed herein may be composited with a porous matrix material, such as silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of finely divided zeolite and inorganic oxide gel matrix may vary widely with the zeolite content ranging from between about 1 to about 99 percent by weight and more usually in the range of about 5 to about 80 percent by weight of the composite.

Methylation of toluene in the presence of the above-described catalyst is effected by contact of the toluene with a methylating agent, preferably methanol, at a temperature between about 300° C. and about 750° C. and preferably between about 400° C. and about 700° C. The reaction generally takes place at atmospheric pressure, but the pressure may be within the approximate range of 1 atmosphere to 1000 psig. The molar ration of methylating agent to toluene is generally between about 0.05 and about 5. When methanol is employed as the methylating agent a suitable molar ratio of methanol to toluene has been found to be approximately 0.1–2 moles of methanol per mole of toluene. With the use of other methylating agents such as methylchloride, methylbromide, dimethylether or dimethylsulfide, the molar ratio or methylating agent to toluene may vary within the aforenoted range. Reaction is suitably accomplished utilizing a weight hourly space velocity as above defined, of between about 1 and about 2000 and preferably between about 5 and about 1500. The reaction product consisting predominantly of para-xylene, and ortho-xylene may be separated by any suitable means, such as by passing the same through a water condenser and subsequently passing the organic phase through a column in which chromatographic separation of the xylene isomers is accomplished.

The process of this invention may be carried out as a batch type, semi-continuous or continuous operation utilizing a fixed or moving bed catalyst system. Multiple injection of the methylating agent, e.g. methanol, may suitably be employed. One embodiment entails use of a fluidized catalyst zone wherein the reactants, i.e. toluene and methylating agent are passed concurrently or countercurrently through a moving fluidized bed of the catalyst. The catalyst after use is regenerated during which time accumulated coke is removed by combustion.

The following examples will serve to illustrate the process of this invention without limiting the same:

EXAMPLE 1

ZSM-23 was prepared by forming a solution of 13.2 grams sodium aluminate (43.1% $Al_2O_3$, 33.1% $Na_2O$ and 24.7% $H_2O$), 2.72 grams NaOH (50% solution with water) and 240 grams $H_2O$. Then, 145.6 grams of pyrrolidine were added, followed by the addition of 1318 grams of colloidal silica (30% silica and 70% $H_2O$). The resulting product was mixed until a homogenous gel was formed. The gel was composed of the following components in mole ratios:

| | |
|---|---|
| $\frac{R^+}{R^+ + M^+}$ | 0.92, where M is sodium and $R^+$ is the nitrogen-containing cation derived from pyrrolidine |
| $\frac{OH^-}{SiO_2}$ | .0265 (not including any contribution of $OH^-$ from pyrrolidine) |
| $\frac{H_2O}{OH^-}$ | 371 (not including any contribution of $OH^-$ from pyrrolidine) |
| $\frac{SiO_2}{Al_2O_3}$ | 118 |

The mixture was stirred at 350° F, for 2 days, during which time crystallization was complete. The product crystals were filtered out of the solution and water washed continuously for approximately 16 hours and then dried at 230° F.

X-ray analysis of the crystalline product showed the crystals to have a diffraction pattern corresponding to Table I. Additional lines showing the presence of trace amounts of unidentified crystalline material were also observed.

Chemical analysis of the crystalline product led to the following compositional figures:

| Composition | Wt. % | Mole Ratio on $Al_2O_3$ Basis |
|---|---|---|
| C | 4.96 | — |
| N | 1.11 | — |
| Na | 0.27 | — |
| $Al_2O_3$ | 1.65 | 1.0 |
| $SiO_2$ | 96.9 | 101 |
| $N_2O$ | | 2.68 |
| $Na_2O$ | | 0.36 |

Physical analysis of the crystalline product after calcination for 16 hours at 1000° F. showed it to have a surface area of 215 m²/gram and adsorption tests (conducted as described hereinabove) provided the following results:

| Adsorption | Wt. % |
|---|---|
| Cyclohexane | 2.1 |
| n-Hexane | 6.1 |
| Water | 4.6 |

69.7 grams of ZSM-23 so prepared were heat treated for 3 hours at 1000° F. in nitrogen and then contacted four times at 180°–200° F. with a 10 weight percent solution of $NH_4Cl$, each contact being for a period of 2 hours. The resulting product having a sodium content of 0.03 weight percent was calcined for 10 hours at 1000° F. and thereafter steamed for 20 hours at 1100° F.

EXAMPLES 2–4

A 2:1 mole ratio of toluene:methanol was passed over a 1 gram sample of the catalyst of Example 1. Reaction conditions and results are set forth in Table II below.

TABLE II

| Example | Temp ° C | WHSV | Toluene Conversion | Xylene/Aromatic Mole Percent | Para Xylene/Total Xylenes |
|---|---|---|---|---|---|
| 2 | 400 | 7.5 | 7.1 | 73 | 73 |
| 3 | 500 | 7.5 | 16.0 | 85 | 54 |
| 4 | 550 | 16.9 | 17.3 | 89 | 65 |

EXAMPLE 5

ZSM-23 in the hydrogen form was prepared by forming a solution of 52.8 grams of sodium aluminate, 10.88 grams of NaOH and 960 grams of water. Then, 582.4 grams of pyrrolidine were added, followed by the addition of 5537.6 grams of colloidal silica in 6872 grams of water. The resulting product was mixed until a homogenous gel was formed.

The mixture was stirred at 350° F. for 3 days, during which time crystallization was complete. The product crystals were filtered out of solution and water washed.

X-ray analysis of the crystalline product showed the crystals to have a diffraction pattern corresponding to Table I.

305 grams of the ZSM-23 so prepared were calcined for 3 hours at 700° F. in nitrogen and then contacted four times at 180°-200° F. with a 10 weight percent solution of $NH_4Cl$ utilizing 10 cc of solution per gram of zeolite, each contact being for a period of 2 hours. The ion exchanged product was then water washed free of chloride, dried at 230° F. and calcined for 10 hours at 1000° F.

EXAMPLES 6-8

A 2:1 mole ratio of toluene:methanol was passed over a 0.3 gram sample of the catalyst of Example 5. Reaction conditions and results are shown in Table III below.

TABLE III

| Example | Temp ° C | WHSV | Toluene Conversion | Xylene/ Aromatic Mole Percent | Para Xylene/ Total Xylenes |
|---|---|---|---|---|---|
| 6 | 400 | 8.8 | 10.9 | 67 | 68 |
| 7 | 500 | 8.8 | 6.2 | 73 | 73 |
| 8 | 550 | 25.1 | 14.5 | 87 | 58 |

EXAMPLE 9

ZSM-23 was prepared by forming a solution of 52.8 grams of sodium aluminate, 10.88 grams of NaOH and 960 grams of water. Then, 582.4 grams of pyrrolidine were added, followed by the addition of 5537.6 grams of collodial silica in 6872 grams of water. The resulting product was mixed until a homogenous gel was formed.

The mixture was stirred at 350° F. for 3 days, during which time crystallization was complete. The product crystals were filtered out of solution and water washed.

X-rays analysis of the crystalline product showed the crystals to have a diffraction pattern corresponding to Table I.

EXAMPLES 10-11

A 2:1 mole ratio of toluene:methanol was passed over a 1 gram sample of the catalyst of Example 9. Reaction conditions and results are set forth in Table IV below.

TABLE IV

| Example | Temp ° C | WHSV | Toluene Conversion | Xylene/ Aromatic Mole Percent | Para Xylene/ Total Xylenes |
|---|---|---|---|---|---|
| 10 | 400 | 7.5 | 8.3 | 76 | 51 |
| 11 | 500 | 7.5 | 11.1 | 83 | 38 |

It will be evident from the above tabulated data that para-xylene was selectively produced in an amount greatly in excess of its equilibrium concentration.

It is to be understood that the foregoing description is merely illustrative of preferred embodiments of the invention of which many variations may be made by those skilled in the art within the scope of the following claims without departing from the spirit thereof.

I claim:

1. A process for the selective production of para xylene which comprises reacting toluene with a methylating agent of a temperature between about 300° C. and about 750° C. in the presence of a catalyst comprising the crystalline aluminosilicate zeolite ZSM-23.

2. The process of claim 1 wherein said methylating agent is methanol, methylchloride, methylbromide, dimethylether or dimethylsulfide.

3. The process of claim 1 wherein said reacting takes place at a weight hourly space velocity of between about 5 and about 1500.

4. The process of claim 1 wherein said methylating agent is methanol.

5. The process of claim 1 wherein said crystalline aluminosilicate zeolite is in the hydrogen form.

6. The process of claim 1 wherein said crystalline aluminosilicate zeolite is used in combination with a porous matrix.

7. The process of claim 1 wherein the molar ratio of methylating agent to toluene is between about .05 and about 5.

8. The process of claim 1 wherein said temperature is between about 400° C. and about 700° C.

9. The process of claim 4 wherein the molar ratio of methanol to toluene is between about 0.1 and about 2.

* * * * *